United States Patent
Malchesky

(10) Patent No.: US 6,558,622 B1
(45) Date of Patent: May 6, 2003

(54) SUB-CRITICAL FLUID CLEANING AND ANTIMICROBIAL DECONTAMINATION SYSTEM AND PROCESS

(75) Inventor: Paul S. Malchesky, Painesville Township, OH (US)

(73) Assignee: Steris Corporation, Mentor, OH (US)

( * ) Notice: Subject to any disclaimer, the term of this patent is extended or adjusted under 35 U.S.C. 154(b) by 0 days.

(21) Appl. No.: 09/674,787

(22) PCT Filed: May 4, 1999

(86) PCT No.: PCT/US99/09770

§ 371 (c)(1),
(2), (4) Date: Nov. 3, 2000

(87) PCT Pub. No.: WO99/56892

PCT Pub. Date: Nov. 11, 1999

(51) Int. Cl.$^7$ ................................. A61L 2/16

(52) U.S. Cl. ............................. 422/28; 422/31; 422/33; 422/62; 422/119; 422/297; 422/305; 210/167; 68/18 R; 68/18 C; 134/6; 134/22.1; 134/22.11; 134/30; 134/95.1; 134/109

(58) Field of Search .................. 422/1, 3–4, 28–29, 422/31–37, 62, 68.1, 101, 103–105, 119, 255–256, 285, 288–289, 292, 295, 297, 300, 305–307; 210/167; 134/6, 8, 10, 19, 22.1, 22.11, 30, 22.12–22.13, 22.18, 22.17, 26, 29, 34, 36, 95.1, 95.3, 109; 68/18 R, 18 C

(56) References Cited

U.S. PATENT DOCUMENTS

| | | | |
|---|---|---|---|
| 4,710,350 A | 12/1987 | Petersen | 422/37 |
| 4,737,384 A | * 4/1988 | Murthy et al. | 427/369 |
| 4,952,370 A | 8/1990 | Cummings et al. | 422/28 |

(List continued on next page.)

FOREIGN PATENT DOCUMENTS

DE  3904513 A  2/1989

OTHER PUBLICATIONS

L. J. Snowden–Swan, *Supercritical Carbon Dioxide Cleaning Market Assessment and Commercialization/Deployment Plan*, Pacific Northwest Laboratory, (Aug. 1994).

Barbara Kanegsberg, "Precision Cleaning Without Ozone Depleting Chemicals," Chemistry and Industry, n20, p. 787 (5) (Oct. 21, 1996) (Full Text).

David Jackson, "Centrifugal–shear Carbon Dioxide Cleaning," Advanced Materials & Processes, v 147, n 5, p 35–36 (May 1995) (abstract only).

(List continued on next page.)

*Primary Examiner*—Robert J. Warden, Sr.
*Assistant Examiner*—Monzer R. Chorbaji
(74) *Attorney, Agent, or Firm*—Fay, Sharpe, Fagan, Minnich & McKee, LLP

(57) ABSTRACT

A chamber (10) is supplied with a pressurized cleaning agent of carbon dioxide and cosolvents from a first source (12) and an antimicrobial fluid, such as ethylene oxide or hydrogen peroxide from a second source (16). Chamber conditions are maintained in the sub-critical range for the carbon dioxide. The cleaning agent and antimicrobial fluid are recirculated through a separator (32) and a condenser (38) to filter contaminants from the mixture before returning the carbon dioxide, and optionally the antimicrobial fluid and other additives, to the chamber. Medical instruments or other articles within the chamber are cleaned by the cleaning agent and sterilized by the antimicrobial fluid in a single cycle, rendering them ready for reuse in a short period of time. The instruments may be cleaned and stored in hermetically sealable containers (82). The cleaning agent is rapidly evaporated from surfaces of the articles at the end of the cycle by reducing the pressure in the chamber. optionally, a vacuum pump (60) assists in removing the antimicrobial fluid from the chamber.

19 Claims, 4 Drawing Sheets

U.S. PATENT DOCUMENTS

| | | | |
|---|---|---|---|
| 5,013,366 A | * 5/1991 | Jackson et al. | 134/1 |
| 5,106,513 A | * 4/1992 | Hong | 210/759 |
| 5,213,619 A | 5/1993 | Jackson et al. | 134/1 |
| 5,232,604 A | * 8/1993 | Swallow et al. | 210/759 |
| 5,236,602 A | * 8/1993 | Jackson | 210/748 |
| 5,267,455 A | 12/1993 | Dewees et al. | 68/5 C |
| 5,288,467 A | 2/1994 | Biermaier | 422/116 |
| 5,344,493 A | 9/1994 | Jackson | 134/1 |
| 5,355,901 A | 10/1994 | Mielnik et al. | 134/105 |
| 5,370,740 A | 12/1994 | Chao et al. | 134/1 |
| 5,401,322 A | 3/1995 | Marshall | 134/13 |
| 5,456,759 A | 10/1995 | Stanford, Jr. et al. | 134/1 |
| 5,505,219 A | 4/1996 | Lansberry et al. | 134/105 |
| 5,526,834 A | 6/1996 | Mielnik et al. | 134/105 |
| 5,552,115 A | 9/1996 | Malchesky | 422/28 |
| 5,759,486 A | 6/1998 | Peterson | 422/21 |
| 5,772,783 A | 6/1998 | Stucker | 134/12 |
| 5,783,082 A | 7/1998 | DeSimone et al. | 210/634 |

OTHER PUBLICATIONS

LIN HM; CAO NJ; CHEN LF, "Antimicrobial Effect of Pressurized Carbon–dioxide on Listeria–monocytogenes," Journal of Food Science, v 59, n 3, p 657–659 (May–Jun. 1994) (abstract only).

Kumagai H.; Hata C; Nakamura K, "CO2 Sorption by Microbial Cells and Sterilization by High–pressure CO2," Bioscience Biotechnology and Biochemistry, v 61, n 6, pp. 931–935 (Jun. 1997) (abstract only).

Smith RE, "Food Demands of the Emerging Consummer: The Role of Modern Food Technology in Meeting that Challenge," Am. J. Clin. Nutr., 58 (2 Suppl), pp. 307s–312s (Aug. 1993).

Mueller B W; Wassmus W, "Preparation of Microparticles from Biodergradable Polymers in Supercritical Gases," Arch.Pharm., 322, No. 10, p 687 (1989) (abstract only).

Lin H–M.; Yang Z.; Chen L.F., "Inactivation of Saccharomyces–cerevisiae by Supercritical and Subcritical Carbon Dioxide," Biotechnol. Prog. 8 (5) pp. 458–461 (1992).

Ishkawa H; Shimoda M; Shiratsuchi H; Osajima Y, "Sterilization of Microorganisms by the Supercritical Carbon Dioxide Micro–bubble Method," Bioscience Biotechnology and Biochemistry, 59 (10) 1949–1950 (1995) (abstract only).

Lin, Ho–mu; Yan, Zhiying; Chen, Li Fu, "Inactivation of Leuconostoc Dextranicum with Carbon Dioxide Under Pressure," Chemical Engineering Journal and Biochemical Engineering Journal, v 52, n 1, pp. B29–B34 (Aug. 1993) (abstract only).

Kobayashi Norio, "Why are Supercritical Fluids Noted Now?," Kogyo Zairyo, vol. 44, No. 9, pp. 102–104, (1996).

* cited by examiner

SUB-CRITICAL FLUID CLEANING AND ANTIMICROBIAL DECONTAMINATION SYSTEM AND PROCESS

BACKGROUND OF THE INVENTION

The present invention relates to the sterilization and disinfection arts. It finds particular application in conjunction with sub-critical fluids associated with antimicrobial agents, such as sterilants or disinfectants, for combined cleaning and sterilization or disinfection of medical instruments, equipment, and supplies, and will be described with particular reference thereto. It should be appreciated, however, that the invention is also applicable to the sterilization or disinfection of other items, including food processing equipment and packaging and hospital supplies, such as bed linen and protective clothing, and the like.

The reusability of medical instruments has become increasingly important in an effort to provide cost-effective health care. Many of the instruments that are now sterilized or disinfected, such as endoscopes, contain tortuous paths, narrow lumens, and other difficult to clean areas. Typically, such instruments are cleaned prior to sterilization or disinfection, to remove organic matter and other dirt which impedes the progress of antimicrobial agents to the surfaces of the instruments. Conventional cleaning methods often fail to remove some of the more heavily adhered or inaccessible organic matter, making it difficult for the antimicrobial agent to effectuate complete decontamination of the instruments in a relatively short period of time. Moreover, workers are exposed to the unsterilized, and sometimes poorly cleaned, instruments when transferring the instruments from the cleaning system to a sterilization or disinfection vessel.

Cleaning systems traditionally use solvents which sometimes leave harmful residues on the instruments or which pose environmental hazards. Water-based cleaning compositions, while tending to be less hazardous, often lead to corrosion of metal parts of the instruments with repeated cleaning. Poor water quality sometimes results in deposits on the instruments or to microbiological contamination. Processing time is often lengthy due to the need for drying the instruments between the cleaning and sterilization or disinfection phases.

Recently, supercritical fluid dry cleaning systems have been developed for cleaning instrument parts and as a replacement for chlorofluorocarbons. A supercritical fluid is a pure compound or mixture which is at a temperature and pressure at or above the critical temperature and pressure of the compound. Carbon dioxide is a particularly advantageous fluid because it is a non-polar solvent. This allows cosolvents to be added having a high degree of selectivity. Cleaning is effectuated more rapidly than for many conventional systems, in part because the fluid rapidly evaporates from the cleaned surfaces when the pressure is reduced. EP 0 679 753 A2 discloses a liquid carbon dioxide dry cleaning system which uses agitation and cleaning enhancers, such as surfactants and solvents, to remove contaminants from garments or fabrics.

Supercritical fluid cleaning systems, however, do not necessarily sterilize or disinfect the instruments. To date, such systems have not been used for cleaning medical instruments, and the like. Where sterilization or disinfection, as well as cleaning, is required, a separate sterilization or disinfection process conventionally increases the processing time and poses hazards to workers handling the unsterilized instruments.

Jackson, et al. (U.S. Pat. No. 5,213,619) discloses a supercritical cleaning process in which chemical oxidizing agents, such as hydrogen peroxide, are transported into a cleaning chamber together with a supercritical fluid. The oxidizing agent is exposed to high energy acoustic radiation to create oxidizing radicals within the supercritical fluid. Other additives, such as surfactants, biocides, and the like, may also be included. WO 96/23606 also to Jackson, discloses a centrifugal separation process which removes dirt from contaminated items in a cleaning process which cycles a dense fluid between a pressure below the critical pressure and one above the critical pressure.

However, the high pressures employed in supercritical cleaning call for specialized equipment capable of withstanding the high pressures.

The present invention provides a new and improved combined cleaning and sterilization or disinfection system and process at sub-critical pressures which overcomes the above referenced problems and others.

SUMMARY OF THE INVENTION

In accordance with one aspect of the present invention, a method for cleaning contaminants from articles and microbially decontaminating the articles is provided. The method includes contacting the articles with a dense cleaning fluid at a sub-critical pressure to remove contaminants from the articles. The method is characterized by, after the step of contacting the articles with a dense cleaning fluid, contacting the articles with an antimicrobial fluid to microbially decontaminate the articles.

In accordance with another aspect of the present invention, a sub-critical fluid cleaning and microbial decontamination system is provided for combined cleaning of contaminants from medical instruments, and killing microbes on the medical instruments. The system includes a chamber which receives the instruments, a source of a dense cleaning fluid, fluidly connected with the chamber, the dense cleaning fluid being one which is gaseous under ambient conditions. A source of an antimicrobial fluid, separate from the source of the dense cleaning fluid, is fluidly connected with the chamber. An injection system connected with the source of cleaning fluid and with the chamber. The injection system supplies pressurized dense cleaning fluid to the chamber at a pressure sufficient for bringing the dense cleaning fluid within the chamber to a sub-critical pressure and separately supplies the antimicrobial fluid to the chamber.

One advantage of the present invention is that it provides a unitary sterilization or disinfection and cleaning process which reduces processing time.

Another advantage of the present invention is that hazards which would otherwise be posed by microbially contaminated instruments during transfer of the instruments between the cleaning and the decontamination systems are eliminated.

Yet another advantage of the present invention is that it employs cleaning fluids which are amenable to non-hazardous disposal after use, without posing significant environmental hazards.

A further advantage of the present invention is that it enables cleaning fluids and antimicrobial agents to be separately recycled.

A yet further advantage of the present invention is that the processing equipment need not withstand supercritical pressures.

A yet still further advantage of the present invention is that it enables heat sensitive instruments to be cleaned without risk of heat damage.

Still further advantages reside in the ability to clean and microbially decontaminate instruments directly after patient use, without prior drying of the instruments.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
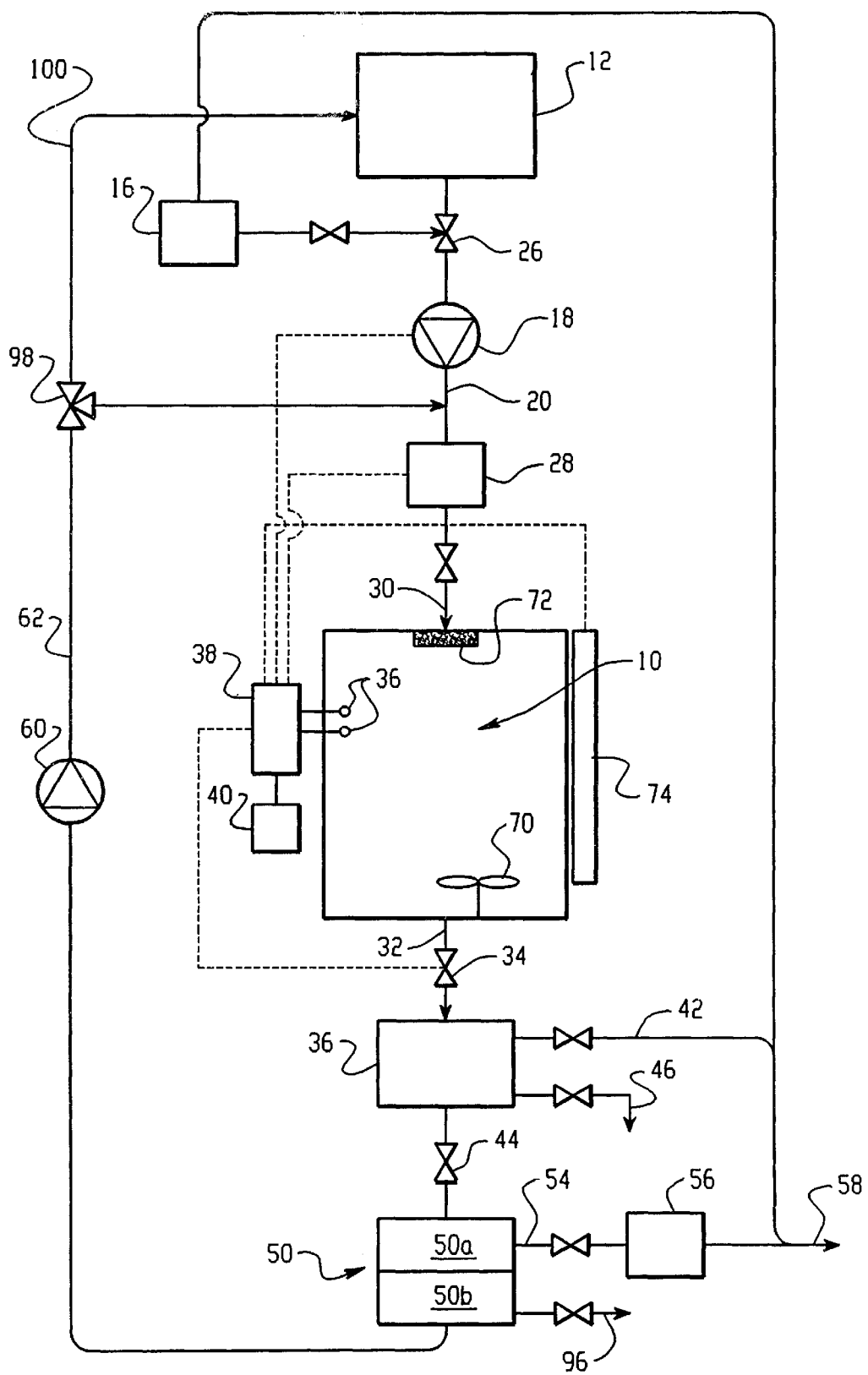
FIG. 1 is a schematic view of a sub-critical cleaning and decontamination system in accordance with the present invention.
Figure 2:
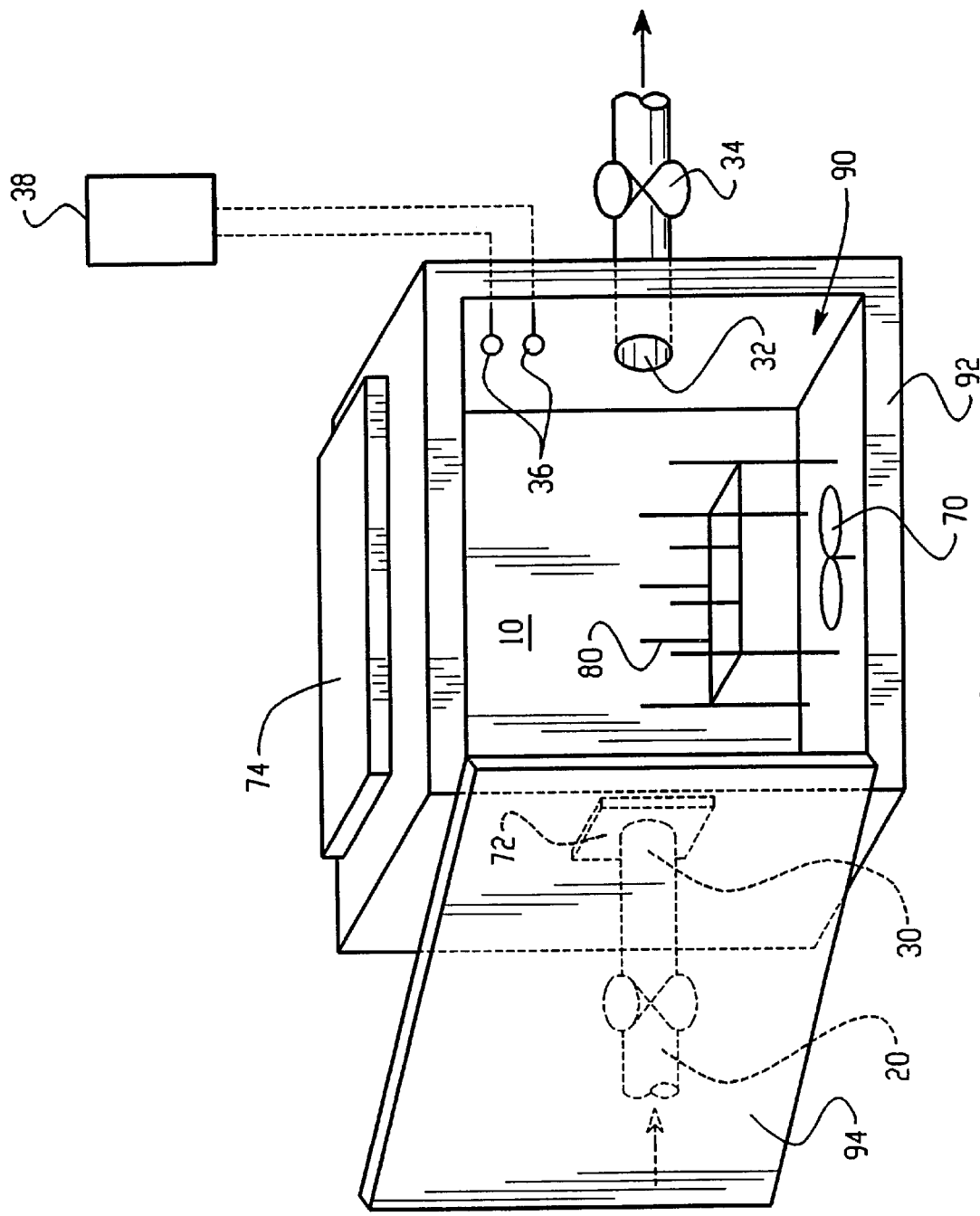
FIG. 2 is a front elevational view of the chamber of FIG. 1.

With reference to FIGS. 1 and 2, a system for sub-critical cleaning and microbial decontamination of articles, such as medical and pharmaceutical instruments, equipment, and the like, includes a combined cleaning and microbial decontamination chamber, such as processing chamber 10, and a source of a dense cleaning fluid, such as a storage vessel 12. The storage vessel maintains the dense cleaning fluid, which is gaseous under ambient conditions, under pressure, preferably in the liquid state. The system also includes a source of antimicrobial agents, preferably an antimicrobial fluid container 16. Optionally, a single storage vessel 12 contains both the dense cleaning fluid and the antimicrobial fluid.

While particular reference is made herein to the use of sterilants for effecting sterilization, it should be appreciated that the system is equally applicable to use with disinfectants for effecting a combined cleaning and disinfection operation. Terms relating to microbial decontamination should be understood also to apply to sterilization, disinfection, and other forms of antimicrobial sanitation.

The system is effective for removing biological wastes, such as blood, urine, and tissue fluids and particles, from medical instruments, surgical devices, and the like. It is particularly suited to cleaning of instruments with complex shapes, such as endoscopes and other instruments with internal passageways. The addition of an antimicrobial fluid to the dense fluid renders the cleaned equipment in a sterilized or disinfected condition and thus the instruments are ready for reuse, without further antimicrobial decontamination.

The gases most suitable as dense cleaning fluids include inorganics, such as carbon dioxide, argon, krypton, xenon, nitrous oxide, oxygen, helium, and mixtures of these.

Supercritical cleaning employs temperatures at or above the critical temperature and pressures at or above the critical pressure. The critical temperature and pressure vary with the gas selected. The critical temperature of a gas is the temperature above which the gas can no longer be liquefied, irrespective of the pressure applied. The critical pressure is the pressure at which a substance may exist as a gas in equilibrium with a liquid at the critical temperature. Thus, the properties of a dense fluid change appreciably at or above the critical pressure.

In contrast, the present invention employs a sub-critical dense cleaning fluid which is in the liquid state. That is, a dense cleaning fluid at a sub-critical pressure and preferably also at a sub-critical temperature, to effect cleaning. By sub-critical pressure, it is meant that the pressure is below the critical pressure for the cleaning fluid. The properties of the dense cleaning fluid are distinctly different below the critical pressure. The preferred sub-critical pressures are those which are up to 95% of the critical pressure, although the pressure can be significantly lower and still achieve dense fluid cleaning. For carbon dioxide, where the critical pressure is 72.9 atmospheres (75 kilograms per square centimeter), preferred sub critical pressures are those which are below about 70 kilograms per square centimeter.

The minimum pressure for cleaning is dependent on the temperature used, since this affects the minimum pressure at which the dense fluid is in the liquid state. At around room temperature, or slightly above (around 20–28° C.), the sub-critical pressure can be as low as about 10% of the critical pressure. For carbon dioxide, this is equivalent to a pressure of about 7–8 kilograms per square centimeter. More preferably, the sub-critical pressure is between about 20 and 90% of the critical pressure, or about 15–65 kilograms per square centimeter for carbon dioxide. For minimizing costs of pressure-withstanding operating equipment while ensuring a fairly rapid cleaning, a particularly preferred sub-critical pressure for carbon dioxide is between 35 and 60 kilograms per square centimeter (about 50–80% of the critical pressure).

Under such pressure conditions, cleaning and decontamination is achieved, without the need for equipment capable of withstanding supercritical pressures.

The temperature of the dense cleaning fluid in the chamber is preferably sub-critical, by which it is meant that the temperature is below the critical temperature, such that the dense fluid is a liquid. For carbon dioxide, which has a critical temperature of around 31° C., preferred temperatures are above the freezing point of water, i.e. 0° C., to avoid freeze cracking of instruments, and up to 30° C. A particularly preferred sub-critical temperature is in the room temperature range to just below the critical temperature, i.e. about 18–30° C. for carbon dioxide. The possibility of damage to heat sensitive medical instruments is minimized in this range. More preferably, the temperature of the dense cleaning fluid is at around room temperature. For carbon dioxide, therefore, the temperature for sub critical cleaning is more preferably between about 18° C. and 25° C. At such temperatures, heating of the vessel is not necessary.

Optionally, the temperature is cycled, for example, by raising the temperature to around the critical temperature and then dropping the temperature.

Instruments to be cleaned and decontaminated are inserted into the chamber 10, and the chamber sealed. The chamber preferably withstands relatively high pressures (7–70 $kg/cm^2$) without leakage, although the use of equipment withstanding only lower pressures, in the 7–20 $kg/cm^2$ range, is also contemplated, allowing for the use of less pressure-resistant equipment. At the beginning of a cleaning and decontamination cycle, a fluid injection system 18, such as a pump, or other delivery system, transfers cleaning fluid from the storage vessel 12 through a fluid flow line 20 to the chamber 10. The injection system preferably also delivers antimicrobial fluid to the chamber from the antimicrobial fluid container 16.

Alternatively, the dense cleaning fluid is provided at high pressure, eliminating the need for a pump.

Figure 3:
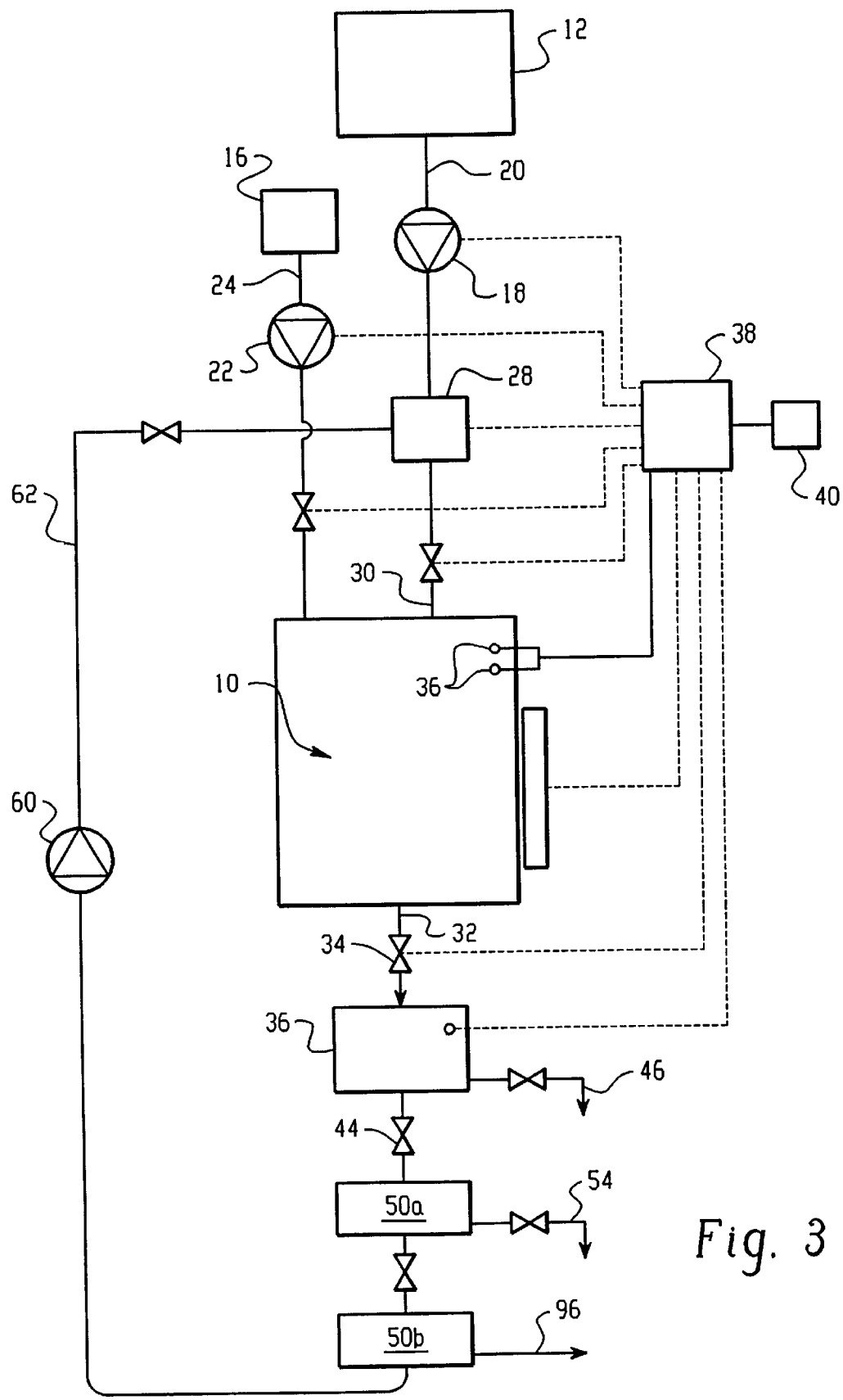
FIG. 3 is a schematic view of an alternative embodiment of a sub-critical cleaning and decontamination system in accordance with the present invention; and, FIG. 4 is a side elevational view of a processing tray in accordance with the present invention.

With reference to FIG. 3, in an alternative embodiment, the antimicrobial fluid and the cleaning fluid are delivered to the chamber by separate injection systems 18 and 22. A separate antimicrobial fluid flow line 24 conveys the antimicrobial fluid into the processing chamber 10.

The separate sources of antimicrobial fluid and cleaning fluid allow for a two-stage cleaning and decontamination process, in which the bulk of the soil present on surfaces of the items is first removed with the sub-critical fluid alone and then the items are decontaminated and further cleaned by the antimicrobial fluid and sub-critical fluid together. Alternatively, the dense cleaning fluid and antimicrobial fluid are introduced contemporaneously, or the antimicrobial fluid is introduced first.

With reference again to FIGS. 1 and 2, appropriate valves, such as a supply valve 26, control the rate and the timing of the addition of cleaning fluid and antimicrobial fluid to the chamber.

A preheater 28, disposed in fluid line 20, heats the cleaning fluid to the selected sub-critical temperature. From the heater, the cleaning and antimicrobial fluids are introduced to the chamber through a fluid inlet 30. The pressure within the chamber is increased through further addition of cleaning fluid, and optionally antimicrobial fluid, until the pre-selected sub-critical conditions are achieved.

Cleaning fluid and antimicrobial fluid are removed from the chamber through a fluid outlet 32. An outlet valve 34 controls the rate and timing of fluid removal.

Monitors 36 detect conditions within the chamber, such as pressure, temperature, and antimicrobial fluid concentration. A control circuit 38 receives signals from the monitors, addresses a look-up table 40, and determines the variation in the detected conditions from preselected chamber conditions. The control circuit signals the pump, preheater, valves 26 and 34, and other appropriate components of the system, to regulate the chamber conditions in accordance with the preselected conditions.

Optionally, the control circuit 38 generates a print-out of the process conditions, such as temperature and pressure, which were monitored throughout the cleaning and decontamination process, or otherwise provides an indication that the process has been appropriately conducted, or not, as the case may be.

Spent cleaning fluid and antimicrobial fluid passes from the outlet valve 34 to a separator 36. The separator filters contaminants, such as organic matter and other dirt, from the cleaning fluid and antimicrobial fluid by evaporation of the antimicrobial fluid and the cleaning fluid. Where the antimicrobial fluid and cleaning fluid have different vapor pressures, the separator optionally fractionates the antimicrobial fluid from the cleaning fluid, allowing the two components to be recovered separately. The antimicrobial fluid is withdrawn through a separator outlet 42. Alternatively, the cleaning fluid and antimicrobial fluid are evaporated together and exit the separator in the gaseous state. A separator valve 44 controls the rate of flow through the separator 36. Filtered organic matter and dirt are periodically removed from the separator through a waste outlet 46.

The cleaning fluid is preferably recirculated through the chamber 10 for further cleaning of the instruments. During the recirculation period, cleaning fluid and antimicrobial fluid, which are free from contaminants, are passed from the separator 36 to a condenser 50 where the fluids are condensed. Where the antimicrobial fluid is a liquid under ambient conditions, it tends to condense before the cleaning fluid, allowing it to be recovered separately, if desired, through an antimicrobial fluid outlet line 54. The spent antimicrobial fluid is collected in an antimicrobial fluid containment vessel 56 and returned to the container 16, or passed directly to a vent 58, where it is optionally destroyed, i.e. converted to non-hazardous components.

Optionally, the condenser includes first and second condenser compartments, or sections 50*a* and 50*b*, respectively. The least volatile component, typically the antimicrobial fluid, is condensed first in the first condenser compartment 50*a* at a relatively low pressure and withdrawn from the first compartment 50*a* through the antimicrobial fluid outlet line 54. The remaining, more volatile component, usually the cleaning fluid, is separately condensed at higher pressure in the second condenser compartment 50*b*. A recirculation pump 60 returns the condensed cleaning fluid to the chamber 10 through a return line 62.

Alternatively, where the spent antimicrobial fluid is a gas under ambient conditions, or when the antimicrobial fluid and cleaning fluid are to be recirculated together through the chamber, a combined antimicrobial fluid and cleaning fluid condensate is returned to the chamber through the return line 62. Preferably, the return line feeds the decontaminated fluid into the fluid flow line 20 at a point before the preheater 28. Alternatively, the fluid is returned directly to the chamber 10.

Preferably, at least some of the cleaning fluid is circulated through the chamber prior to introduction of antimicrobial fluid. Organic matter deposited on the instruments is removed from the instruments by the cleaning fluid and then leaves the chamber through the outlet 32. This reduces the amount of organic material in the chamber which otherwise could lead to a partial inactivation of the antimicrobial fluid. The preferred timing of addition of the antimicrobial fluid, however, is also dependent on other factors, such as the natural state of the antimicrobial fluid, either solid, liquid, or gaseous, the ease of introducing the antimicrobial fluid into the chamber, and the degree of miscibility of the antimicrobial fluid in the cleaning fluid. Therefore, the antimicrobial fluid is optionally introduced at the same time, or prior to, addition of the cleaning fluid.

With particular reference to FIG. 2, an impeller 70, within the chamber 10, circulates the cleaning fluid and antimicrobial fluid throughout the chamber and over the instruments to be cleaned and decontaminated. Optionally, a filter 72 filters cleaning fluid and antimicrobial fluid entering the chamber. A heater 74 heats the chamber to maintain the cleaning fluid in the cleaning fluid within the critical or sub critical range.

A support system 80 supports instruments to be cleaned and sterilized or disinfected within the chamber 10. The support system is constructed so as to provide ready access to the surfaces of the instruments for the cleaning fluid and the antimicrobial fluid. Depending on the nature of the instruments to be decontaminated, racks, shelves or mesh baskets provide suitable support systems. A rigid, open-celled porous media, such as POREX brand expanded polymer material, is optionally used for holding the instruments securely, while at the same time permitting the antimicrobial fluid and the cleaning fluid to penetrate to the surfaces of the instruments.

Figure 4:
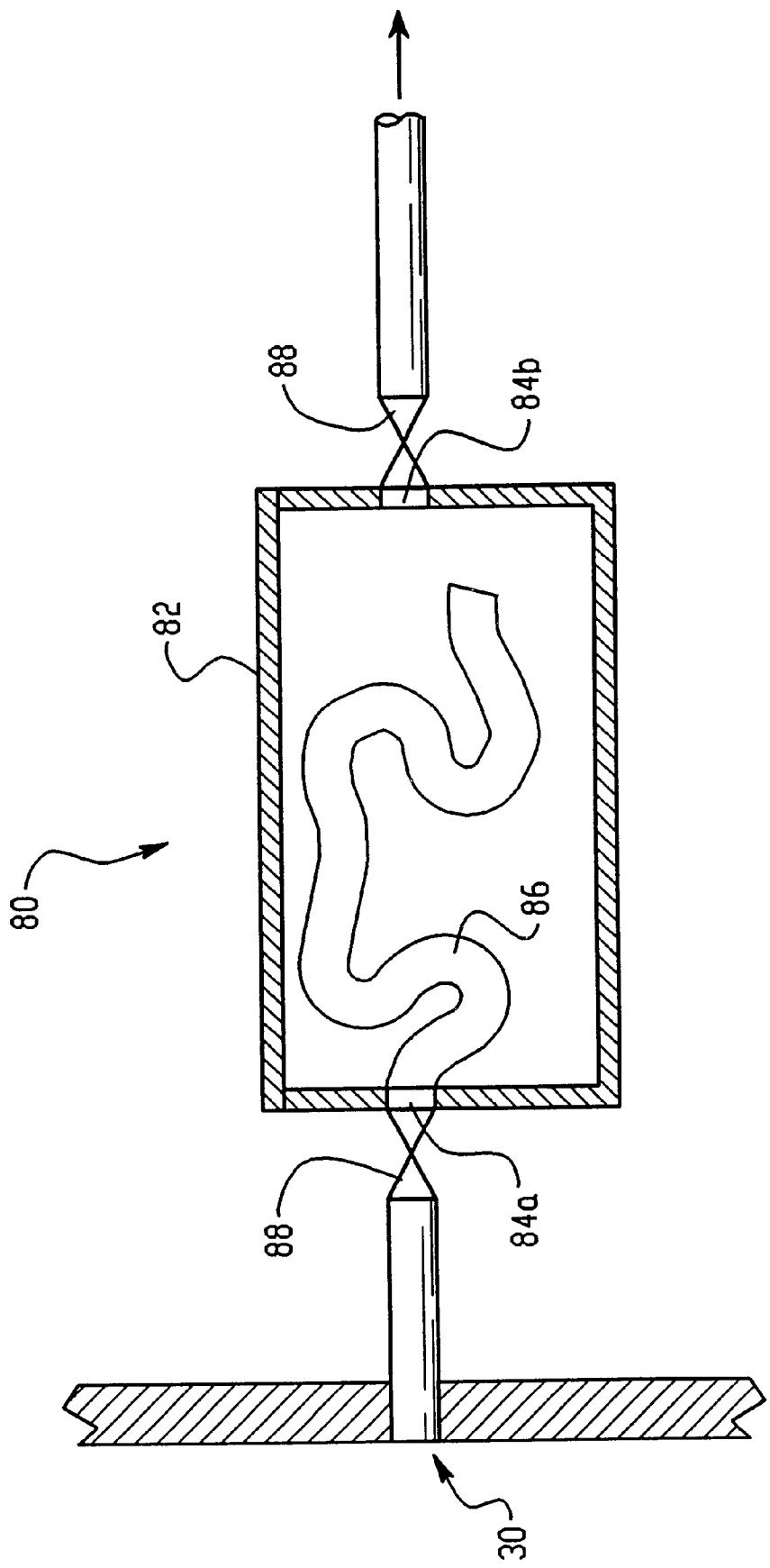

With reference to FIG. 4, a preferred support system for maintaining sterility of decontaminated items includes an enclosed tray 82. Instruments to be cleaned and sterilized or disinfected are inserted into a bottom portion of the tray. A cover portion covers the bottom portion. The cleaning fluid and antimicrobial fluid enter and leave the tray through inlet and outlet openings 84a and 84b in the tray. Optionally one of the openings is fluidly connected directly or via a manifold to an interior passage 86 of one or more instruments to be sterilized or disinfected. Cleaning fluid and antimicrobial fluid enters the tray through inlet opening 84a and passes through the interior passage of the instrument and around exterior surfaces of the instrument before exiting the tray through outlet 84b. In this manner, the interior of the instrument is cleaned first with the freshest fluid. When cleaning and decontamination of the exterior is paramount, the flow pattern is reversed.

Sealing members 88 selectively hermetically seal the tray openings 84a and 84b once cleaning and sterilization or disinfection are complete. The members 88 include check valves, baffles, or other structures which block ambient microbes from entering the tray after it is disconnected from the decontamination system. The instruments are then preferably stored in the sealed trays until needed, to avoid unnecessary handling and contamination of the sterilized or disinfected instruments.

With particular reference again to FIG. 2, the instruments, or other items to be decontaminated, are introduced to the chamber through an inlet opening 90 in a side wall 92 of the chamber 10. The instruments need not necessarily be dried before cleaning and decontamination since a small amount of water in the chamber does not appreciable affect the achievement of sub-critical conditions, and also may serve as a cosolvent for improving miscibility of the antimicrobial fluid, and other additives, with the cleaning fluid. A door 94 seals the opening during cleaning and decontamination.

The cleaning fluid preferably includes carbon dioxide. Carbon dioxide has a supercritical temperature of around 31° C., thereby allowing for cleaning at temperatures close to ambient. Optionally, other additives, which may include surfactants, or cosolvents, such as alcohol, acetone, or water, and detergents, are added to the cleaning fluid to enhance cleaning, increase penetration into the instruments, and improve miscibility between the cleaning fluid and the antimicrobial fluid. Particularly when the contaminants on the instruments include polar compounds, surfactants improve extraction of the contaminants from the instruments that are cleaned and decontaminated. These additives may be recycled through the chamber, as for the anti-microbial fluid, or sent for disposal.

The antimicrobial fluid is one which is compatible with the cleaning fluid and which is not appreciably degraded under temperatures and pressures used to provide sub-critical conditions. The antimicrobial fluid preferably acts as an alkylating or oxidizing agent and kills microorganisms typically found on the instruments. Ethylene oxide, propylene oxide, and hydrogen peroxide are preferred antimicrobial fluids. Other antimicrobial fluids include aldehydes, such as formaldehyde or glutaraldehyde, ozone, chlorine, chlorine dioxide, hypochlorites, peracetic acid, other peroxy compounds, and the like. When hydrogen peroxide or peracetic acid is the antimicrobial fluid, it may be combined with water or used in a pure form. Optionally, combinations of antimicrobial fluids are employed.

In operation, preheated, pressurized carbon dioxide, or other cleaning fluid, is pumped into the chamber 10 through the inlet 30 until a sufficient volume is present to maintain the desired pressure. Surfactants are added together with the cleaning fluid from the source of cleaning fluid 12, or separately, from a separate source. The temperature within the chamber is maintained by the heater 74. The control circuit 38 controls the addition of carbon dioxide and the heater to achieve the desired sub-critical conditions. The impeller 70 ensures circulation throughout the chamber. The outlet valve 34 and the pump 18 are controlled to maintain the pressure in the chamber 10 during a cleaning and decontamination cycle.

In a preferred cycle, the cleaning fluid is circulated within the chamber for a period sufficient to clean the instruments. The antimicrobial fluid is then introduced to the cleaning fluid and flowed through the chamber to effect sterilization or disinfection. The cleaning fluid, and optionally the antimicrobial fluid, is preferably recirculated through the chamber via the separator and condenser to remove contaminants from the chamber. The separator valve 42 controls the pressure within the separator so that the exiting cleaning fluid and antimicrobial fluid, where present, are substantially free of contaminants.

After a period of recirculation sufficient to effect decontamination, the inlet 30 is closed by sealing appropriate valves, such as the valve 26. The cleaning fluid and antimicrobial fluid are removed from the chamber 10 by creating a pressure differential between the separator and the chamber. As the pressure drops within the chamber, the carbon dioxide, and other cleaning and decontamination compounds which are gaseous under ambient conditions, rapidly evaporate from the decontaminated items and pass out of the chamber into the separator 36. The spent antimicrobial fluid is preferably discharged through the waste line 46 or the spent antimicrobial fluid line 54 to the containment vessel 56. Optionally, the antimicrobial fluid is recovered for reuse. The carbon dioxide is either vented to the atmosphere from the condenser 50 through a vent line 96 or, more preferably, returned to the cleaning fluid supply vessel through the return line 62. A three way valve 98 selectively directs the cleaning fluid from the return line 48 to the fluid flow line 20 for return to the chamber 10, or to a reclaim line 100 for return to the cleaning fluid storage vessel 12.

The cosolvents, and other additives present, may be cleaned and recycled, or discharged with the spent antimicrobial fluid. In one embodiment, additives are separated from contaminants by evaporation, vapor phase separation, filtration, or other separation method and returned to the chamber.

Optionally, the chamber 10 is evacuated prior to addition of the cleaning fluid and antimicrobial fluid. The pump 60, or another suitable pump, is employed for the evacuation. Additionally, evacuation of the chamber following decontamination ensures that potentially harmful antimicrobial fluids, surfactants, cleaning agents, other volatile compounds, and the like, are removed from the instruments to reduce the risk of contamination of patients.

Having thus described the preferred embodiment, the invention is now claimed to be:

1. A method for cleaning contaminants which include biological or bodily fluids from medical or pharmaceutical instruments and disinfecting or sterilizing the medical or pharmaceutical instruments, including:

contacting the medical or pharmaceutical instruments with a dense cleaning fluid for a sufficient period of time and at a sub-critical pressure to remove biological contaminants and body fluids from the medical or pharmaceutical instruments; and after the step of contacting the articles with a dense cleaning fluid, disinfecting or sterilizing the medical or pharmaceutical instruments by replacing the contaminated dense cleaning fluid with an antimicrobial fluid and contacting the medical or pharmaceutical instruments with the antimicrobial fluid to disinfect or sterilize the medical or pharmaceutical instruments, until the instruments are rendered suitable for surgical procedures or for introduction to the human body.

2. The method of claim 1, wherein the step of contacting the medical instruments with an antimicrobial fluid further includes:

simultaneously contacting the medical instruments with a dense cleaning fluid.

3. The method of claim 1, wherein the dense fluid is in a liquid state.

4. The method of claim 1, wherein the pressure of the dense cleaning fluid is 10–95% of a critical pressure of the dense cleaning fluid.

5. The method of claim 4, wherein the pressure of the dense cleaning fluid is 20–90% of the critical pressure of the dense cleaning fluid.

6. The method of claim 1, wherein the dense cleaning fluid is selected from the group consisting of carbon dioxide, argon, krypton, xenon, nitrous oxide, oxygen, helium, and combinations thereof.

7. The method of claim 6, wherein the dense cleaning fluid is carbon dioxide and the pressure is between 7 and 70 kilograms per square centimeter.

8. The method of claim 1, wherein the dense cleaning fluid is at a temperature between the freezing point of water and the critical temperature of the dense cleaning fluid.

9. The method of claim 8, wherein the dense cleaning fluid is carbon dioxide and the temperature is from about 18° C. to 30° C.

10. The method of claim 1, wherein the antimicrobial fluid is selected from the group consisting of ethylene oxide, propylene oxide, hydrogen peroxide, aldehydes, chlorine dioxide, hypochlorites, peracetic acid, peroxy compounds, ozone, and combinations thereof.

11. The method of claim 1, further including:

evaporating a portion of the dense cleaning fluid which has removed some of the contaminants from the medical or pharmaceutical instruments to separate the dense cleaning fluid from the contaminants;

pressurizing the evaporated cleaning fluid to form a purified dense cleaning fluid; and contacting the medical or pharmaceutical instruments with the purified dense cleaning fluid.

12. The method of claim 11, wherein:

the step of evaporating a portion of the dense cleaning fluid further including evaporating a portion of the antimicrobial fluid; and the step of pressurizing the evaporated cleaning fluid further including pressurizing the evaporated antimicrobial fluid.

13. A method for cleaning biological contaminants from medical or pharmaceutical equipment and microbially decontaminating the cleaned medical or pharmaceutical equipment, including:

cleaning the medical or pharmaceutical equipment with a dense cleaning fluid at a sub-critical pressure, the pressure of the dense cleaning fluid being from 50–80% of the critical pressure of the dense cleaning fluid, to remove the biological contaminants from the medical or pharmaceutical equipment; and contacting the medical or pharmaceutical equipment with the antimicrobial fluid to microbially decontaminate the medical or pharmaceutical equipment.

14. A method for cleaning and microbially decontaminating medical or pharmaceutical equipment, including:

cleaning the medical or pharmaceutical equipment with a dense cleaning fluid at a sub-critical pressure to remove contaminants from the medical or pharmaceutical equipment; and after the step of cleaning the medical or pharmaceutical equipment with a dense cleaning fluid, contacting the medical or pharmaceutical equipment with an antimicrobial fluid with at least one additive selected from the group consisting of surfactants, cosolvents, and detergents to microbially decontaminate the medical or pharmaceutical equipment.

15. The method of claim 12, wherein the step of contacting the medical or pharmaceutical equipment with an antimicrobial fluid further includes:

separating at least a portion of the additive from contaminants removed from the medical or pharmaceutical equipment; and contacting the medical or pharmaceutical equipment with the separated portion of the additive.

16. A method for cleaning contaminants from a medical or pharmaceutical instrument and disinfecting or sterilizing the medical or pharmaceutical instrument, comprising:

inserting a medical or pharmaceutical instrument in an enclosed tray, the tray including an inlet and an outlet;

contacting the medical or pharmaceutical instrument with a dense cleaning fluid for a sufficient period of time and at a sub-critical pressure to remove contaminants from the medical or pharmaceutical instrument, including:

flowing the cleaning fluid through the inlet of the tray, over surfaces of the medical or pharmaceutical instrument, and out through the outlet of the tray; and after the step of contacting the medical or pharmaceutical instrument with a dense cleaning fluid, replacing the contaminated dense cleaning fluid with an antimicrobial fluid and contacting the medical or pharmaceutical instrument with the antimicrobial fluid to disinfect or sterilize the medical or pharmaceutical instrument, including:

flowing the antimicrobial fluid through the inlet of the tray, over surfaces of the medical or pharmaceutical instrument, and out through the outlet of the tray.

17. A method for cleaning contaminants from medical instruments having undergone a surgical procedure and microbially decontaminating the medical instruments, comprising:

contacting the medical instruments with a dense cleaning fluid at a sub-critical pressure to remove contaminants from the medical instruments;

after the step of contacting the medical instruments with a dense cleaning fluid, microbially decontaminating the medical instruments by contacting the medical instruments with an antimicrobial fluid to microbially decontaminate the medical instruments; and after the step of microbially decontaminating the medical instruments with an antimicrobial fluid, removing the dense cleaning fluid and the antimicrobial fluid and subjecting the medical instruments to a vacuum to remove fluid residue.

18. A sub-critical fluid cleaning and microbial decontamination system for combined cleaning of contaminants from medical instruments, and killing microbes on the medical instruments, the system comprising:

a chamber which receives the instruments;

a source of a dense cleaning fluid fluidly connected with the chamber, the dense cleaning fluid being one which is gaseous under ambient conditions;

a source of an antimicrobial fluid fluidly connected with the chamber;

an injection system connected with the source of cleaning fluid and with the chamber;

the injection system supplying pressurized dense cleaning fluid to the chamber at a pressure sufficient for bringing the dense cleaning fluid within the chamber to a sub-critical pressure and separately supplying the antimicrobial fluid to the chamber; and a support system for supporting the medical instruments in the chamber, the support system being partially formed from porous media which is permeable to the cleaning fluid and the antimicrobial fluid.

19. A method for cleaning contaminants from medical or pharmaceutical equipment and microbially decontaminating the medical or pharmaceutical equipment, including:

(a) contact cleaning the medical or pharmaceutical equipment with a dense cleaning fluid at a sub-critical pressure to remove contaminants from the medical or pharmaceutical equipment; and (b) after the step of contact cleaning the medical or pharmaceutical equipment with a dense cleaning fluid, contacting the medical or pharmaceutical equipment with an antimicrobial fluid to microbially decontaminate the medical or pharmaceutical equipment, the antimicrobial fluid being selected from the group consisting of ethylene oxide, propylene oxide, aldehydes, chlorine dioxide, hypochlorites, peracetic acid, and combinations thereof, the antimicrobial fluid being used in step (b) but not in step (a).

* * * * *